US010112173B2

(12) United States Patent
Bouvier et al.

(10) Patent No.: US 10,112,173 B2
(45) Date of Patent: Oct. 30, 2018

(54) ZEOLITE-BASED ADSORBENTS BASED ON ZEOLITE X WITH A LOW BINDER CONTENT AND A LOW OUTER SURFACE AREA, PROCESS FOR PREPARING THEM AND USES THEREOF

(71) Applicants: IFP ENERGIES NOUVELLES, Rueil-Malmaison (FR); ARKEMA FRANCE, Colombes (FR)

(72) Inventors: Ludivine Bouvier, Orthez (FR); Cécile Lutz, Gan (FR); Catherine Laroche, Charly (FR)

(73) Assignees: Arkema France, Colombes (FR); IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 15/526,081

(22) PCT Filed: Nov. 13, 2015

(86) PCT No.: PCT/EP2015/076531

§ 371 (c)(1),
(2) Date: May 11, 2017

(87) PCT Pub. No.: WO2016/075280

PCT Pub. Date: May 19, 2016

(65) Prior Publication Data

US 2017/0304799 A1 Oct. 26, 2017

(30) Foreign Application Priority Data

Nov. 13, 2014 (FR) ...................................... 14 60955

(51) Int. Cl.

| | |
|---|---|
| ***B01J 20/18*** | (2006.01) |
| ***B01J 20/28*** | (2006.01) |
| ***B01J 20/30*** | (2006.01) |
| ***C07C 29/76*** | (2006.01) |
| ***C07C 37/82*** | (2006.01) |
| ***C07C 7/13*** | (2006.01) |
| *B01D 15/18* | (2006.01) |

(52) U.S. Cl.

CPC ............. *B01J 20/186* (2013.01); *B01J 20/18* (2013.01); *B01J 20/183* (2013.01); *B01J 20/2803* (2013.01); *B01J 20/2809* (2013.01); *B01J 20/28057* (2013.01); *B01J 20/28059* (2013.01); *B01J 20/28071* (2013.01); *B01J 20/28085* (2013.01); *B01J 20/28088* (2013.01); *B01J 20/28092* (2013.01); *B01J 20/3028* (2013.01); *B01J 20/3042* (2013.01); *B01J 20/3071* (2013.01); *B01J 20/3085* (2013.01); *C07C 7/13* (2013.01); *C07C 29/76* (2013.01); *C07C 37/82* (2013.01); *B01D 15/1821* (2013.01)

(58) Field of Classification Search

CPC ........ B01J 20/18; B01J 20/183; B01J 20/186; B01J 20/2803; B01J 20/28057; B01J 20/28059; B01J 20/28071; B01J 20/28085; B01J 20/28088; B01J 20/2809; B01J 20/28092; B01J 20/3028; B01J 20/3042; B01J 20/3071; B01J 20/3085

See application file for complete search history.

(56) References Cited

U.S. PATENT DOCUMENTS

| | | | |
|---|---|---|---|
| 2,985,589 | A | 5/1961 | Broughton et al. |
| 3,558,730 | A | 1/1971 | Neuzil |
| 3,558,732 | A | 1/1971 | Neuzil |
| 3,626,020 | A | 12/1971 | Neuzil |
| 3,663,638 | A | 5/1972 | Neuzil |
| 4,402,832 | A | 9/1983 | Gerhold |
| 4,498,991 | A | 2/1985 | Oroskar |
| 5,284,992 | A | 2/1994 | Hotier et al. |
| 5,629,467 | A | 5/1997 | Hotier et al. |
| 6,884,918 | B1 | 4/2005 | Plee et al. |

(Continued)

FOREIGN PATENT DOCUMENTS

| | | | |
|---|---|---|---|
| CN | 1267185 | C | 8/2006 |
| EP | 1142622 | A2 | 10/2001 |

(Continued)

OTHER PUBLICATIONS

Li et al., "Preparation of granular X-type zeolite/activated carbon composite from elutrilithe by adding pitch and solid SiO2," Materials Chemistry and Physics 147 (2014) 1003-1008.*

(Continued)

*Primary Examiner* — Pancham Bakshi
*Assistant Examiner* — Mark R Luderer
(74) *Attorney, Agent, or Firm* — RatnerPrestia

(57) ABSTRACT

The invention relates to an adsorbent comprising a zeolite-based phase and a non-zeolite-based phase, said adsorbent having:

- an outer surface area of less than or equal to 30 $m^2 \cdot g^{-1}$, preferably less than or equal to 20 $m^2 \cdot g^{-1}$,
- a zeolite-based phase comprising at least one zeolite of FAU structure of X type,
- and a pore diameter distribution, determined by mercury intrusion according to standard ASTM D 4284-83 and expressed by the volume distribution dV/dlogDHg, in which DHg is the apparent pore diameter and V is the pore volume, the mode of which is between 100 nm and 250 nm, limits inclusive.

The invention also relates to a process for preparing the said adsorbent and to the uses thereof, especially for separating xylene isomers.

21 Claims, 1 Drawing Sheet

(56) References Cited

U.S. PATENT DOCUMENTS

| | | | |
|---|---|---|---|
| 7,785,563 | B2 | 8/2010 | Ryoo et al. |
| 8,283,274 | B2 | 10/2012 | Cheng et al. |
| 2009/0326308 | A1 | 12/2009 | Kulprathipanja et al. |
| 2012/0093715 | A1 | 4/2012 | Wang |
| 2012/0247334 | A1 | 10/2012 | Hurst et al. |
| 2014/0086817 | A1 | 3/2014 | Brandt et al. |
| 2015/0306565 | A1 | 10/2015 | Bouvier et al. |

FOREIGN PATENT DOCUMENTS

| | | | |
|---|---|---|---|
| FR | 2789914 | A1 | 8/2000 |
| WO | 2007043731 | A1 | 4/2007 |
| WO | 2008009845 | A1 | 1/2008 |
| WO | 2013106816 | A1 | 7/2013 |
| WO | 2014090771 | A1 | 6/2014 |

OTHER PUBLICATIONS

Verboekend, D., et al., "Hierarchical FAU- and LTA-Type Zeolites by Post-Synthetic Design: A New Generation of Highly Efficient Base Catatysts," Apr. 19, 2013, pp. 1923-1934, vol. 23(15), Advanced Functional Materials, DOI: 10.1002/adfm.201202320.

Inayat, A., et al., "Assemblies of Mesoporous FAU-Type Zeolite Nanosheets," Feb. 20, 2012, pp. 1962-1965, vol. 51(8), Angewandte Chemie International Edition, DOI: 10.1002/anie.201105738.

Li, Z., et al., "Preparation of granular X-type zeolite/actived carbon composite from elutrilithe by adding pitch and solid $SiO_2$", Jul. 15, 2014, pp. 1003-1008, vol. 147(3), Materials Chemistry and Physics, DOI: 10.1016/J.matchemphys.2014.06.051.

Michels, N.L., et al., "Hierarchically structured Zeolite Bodies: Assembling Micro-, Meso-, and Macroporosity Levels in Complex Materials with Enhanced Properties," Jun. 20, 2012, pp. 2509-2518, vol. 22(12), Advanced Functional Materials, DOI: 10.1002/ADFM.201103120 [retrieved on Mar. 21, 2012].

International Search Report and Written Opinion for International Application No. PCT/EP2015/076531, dated Mar. 8, 2016—11 Pages.

Ruthven, D., "Principles of Adsorption and Adsorption Processes", John Wiley & Sons, 1984, pp. 243, 248-250, 326, and 407—453 Pages.

Verboekend et al. "Hierarchical Y and USY Zeolites Designed by Post-Synthetic Stragegies", 2012, Adv. Funct. Mater., vol. 22, pp. 916-928.

* cited by examiner

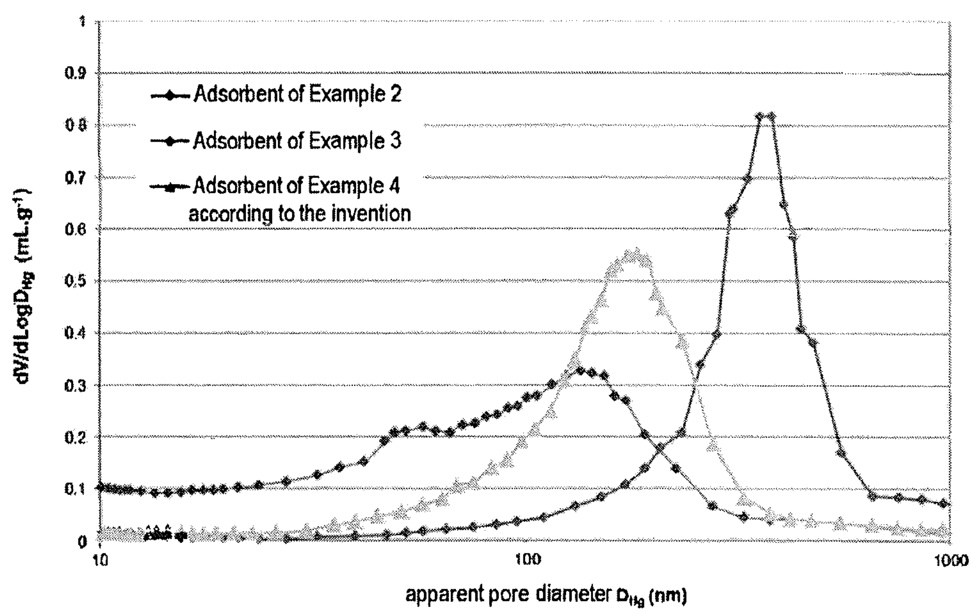
Adsorbent of Example 2
Adsorbent of Example 3
Adsorbent of Example 4 according to the invention
dV/dLogD$_{Hg}$ (mL.g$^{-1}$)
1
0.9
0.8
0.7
0.6
0.5
0.4
0.3
0.2
0.1
0
10
100
1000
apparent pore diameter D$_{Hg}$ (nm)

ZEOLITE-BASED ADSORBENTS BASED ON ZEOLITE X WITH A LOW BINDER CONTENT AND A LOW OUTER SURFACE AREA, PROCESS FOR PREPARING THEM AND USES THEREOF

CROSS-REFERENCE TO RELATED APPLICATIONS

This application is a U.S. National Phase Application of PCT International Application No. PCT/EP2015/076531, filed Nov. 13, 2015 and published May 19, 2016 as WO 2016/075280, which claims priority from French Application No. 1460955 filed Nov. 13, 2014; each of the aforementioned applications is incorporated herein by reference in its entirety for all purposes.

BACKGROUND OF THE INVENTION

The invention relates to zeolite-based adsorbents in the form of agglomerates with a low binder content comprising faujasite zeolite, for their uses in applications in which mass transfer is an important parameter, said adsorbents having a low outer surface area, typically less than or equal to 30 $m^2 \cdot g^{-1}$, preferably less than or equal to 20 $m^2 \cdot g^{-1}$.

The present invention also relates to a process for preparing said zeolite-based adsorbents, and also to the uses thereof, especially for separating gaseous or liquid mixtures of isomers, more particularly of xylenes and especially for producing very pure para-xylene from an aromatic hydrocarbon feedstock containing isomers containing 8 carbon atoms.

The use of zeolite-based adsorbents comprising at least faujasite (FAU) zeolite of X or Y type and comprising, besides sodium cations, barium, potassium or strontium ions, alone or as mixtures, for selectively adsorbing para-xylene in a mixture of aromatic hydrocarbons, is well known from the prior art.

U.S. Pat. Nos. 3,558,730, 3,558,732, 3,626,020 and 3,663,638 show that zeolite-based adsorbents comprising aluminosilicates based on sodium and barium (U.S. Pat. No. 3,960,774) or based on sodium, barium and potassium, are efficient for separating para-xylene present in C8 aromatic fractions (fractions comprising aromatic hydrocarbons containing 8 carbon atoms).

In the patents listed above, the zeolite-based adsorbents are in the form of crystals in powder form or in the form of agglomerates predominantly consisting of zeolite powder and up to 20% by weight of inert binder.

The synthesis of FAU zeolites is usually performed by nucleation and crystallization of silicoaluminate gels. This synthesis leads to crystals (generally in powder form) whose use at the industrial scale is particularly difficult (substantial losses of feedstocks during the manipulations). Agglomerated forms of these crystals are then preferred, in the form of grains, strands and other agglomerates, these said forms possibly being obtained by extrusion, pelleting, atomization and other agglomeration techniques known to those skilled in the art. These agglomerates do not have the drawbacks inherent in pulverulent materials.

Agglomerates, whether they exist in the form of platelets, beads, extrudates or the like, generally consist of zeolite crystals, which constitute the active element (in the sense of adsorption) and of an agglomeration binder. This agglomeration binder is intended to ensure the cohesion of the crystals to each other in the agglomerated structure, but must also give said agglomerates sufficient mechanical strength so as to prevent, or at the very least to minimize, the risks of fractures, splitting or breaks that may arise during their industrial uses during which the agglomerates are subjected to numerous stresses, such as vibrations, high and/or frequent pressure variations, movements and the like.

The preparation of these agglomerates is performed, for example, by pasting zeolite crystals in powder form with a clay paste, in proportions of the order of 80% to 90% by weight of zeolite powder for 20% to 10% by weight of binder, followed by forming into beads, platelets or extrudates, and heat treatment at high temperature for baking of the clay and reactivation of the zeolite, the cation exchange (s), for instance the exchange with barium and optionally with potassium, possibly being performed before and/or after the agglomeration of the pulverulent zeolite with the binder.

Zeolite-based substances are obtained, the particle size of which is a few millimetres, or even of the order of a millimetre, and which, if the choices of the agglomeration binder and the granulation are made according to the rules of the prior art, have a satisfactory set of properties, in particular of porosity, mechanical strength and abrasion resistance. However, the adsorption properties of these agglomerates are obviously reduced relative to the starting active powder due to the presence of agglomeration binder which is inert with respect to adsorption.

Various means have already been proposed for overcoming this drawback of the agglomeration binder being inert as regards the adsorption performance, among which is the transformation of all or at least part of the agglomeration binder into zeolite that is active from the adsorption viewpoint. This operation is now well known to those skilled in the art, for example under the name "zeolitization". To perform this operation readily, zeolitizable binders are used, usually belonging to the kaolinite family, and preferably precalcined at temperatures generally between 500° C. and 700° C.

Patent FR 2 789 914 describes a process for manufacturing zeolite X agglomerates, with an Si/Al atomic ratio of between 1.15 and 1.5, exchanged with barium and optionally with potassium, by agglomerating zeolite X crystals with a binder, a source of silica and carboxymethylcellulose, followed by zeolitizing the binder by immersing the agglomerate in an alkaline liquor. After exchanging the cations of the zeolite with barium ions (and optionally potassium ions) and activation, the agglomerates thus obtained have identical selectivity results as regards the adsorption of para-xylene with respect to other C8 aromatic molecules and an increase in the para- xylene adsorption capacity, relative to adsorbents prepared from the same amount of zeolite X and binder, but whose binder is not zeolitized. Patent FR 2 789 914 thus teaches that the zeolitization of the binder allows an increase in the para-xylene adsorption capacity, without modifying the adsorption selectivity properties.

Besides high adsorption capacity and good selectivity properties with respect to the species to be separated from the reaction mixture, the adsorbent must have good mass transfer properties so as to ensure a sufficient number of theoretical plates to perform efficient separation of the species in admixture, as indicated by Ruthven in the book entitled *Principles of Adsorption and Adsorption Processes*, John Wiley & Sons, (1984), pages 326 and 407. Ruthven indicates (ibid., page 243) that, in the case of an agglomerated adsorbent, the global mass transfer depends on the sum of the intra-crystalline and inter-crystalline (between crystals) diffusional resistances.

The intra-crystalline diffusional resistance is proportional to the square of the diameters of the crystals and inversely proportional to the intra-crystalline diffusivity of the molecules to be separated. The inter-crystalline diffusional resistance (also known as the "macropore resistance") is itself proportional to the square of the diameters of the agglomerates, inversely proportional to the porosity contained in the macropores and mesopores (i.e. the pores with an aperture greater than 2 nm) in the agglomerate, and inversely proportional to the diffusivity of the molecules to be separated in this porosity.

The size of the agglomerates is an important parameter during the use of the adsorbent in industrial application, since it determines the loss of feedstock in the industrial unit and the filling uniformity. The particle size distribution of the agglomerates must thus be narrow, and centred on number-mean diameters typically between 0.40 mm and 0.65 mm so as to avoid excessive losses of feedstock.

The porosity contained in the macropores and mesopores in the agglomerate (the inter-crystalline macroporosity and mesoporosity, respectively) may be increased by using pore-forming agents, for instance corn starch as recommended in document U.S. Pat. No. 8,283,274 for improving the mass transfer. However, this porosity does not participate in the adsorption capacity and consequently the improvement in the macropore mass transfer then takes place to the detriment of the volume-based adsorption capacity. Consequently, this route for improving the macropore mass transfer proves to be very limited.

To estimate the improvement in transfer kinetics, it is possible to use the plate theory described by Ruthven in *Principles of Adsorption and Adsorption Processes, ibid.*, pages 248-250. This approach is based on the representation of a column by a finite number of ideally stirred hypothetical reactors (theoretical stages). The equivalent height of theoretical plates is a direct measurement of the axial dispersion and of the resistance to mass transfer of the system.

For a given zeolite-based structure, a given size of adsorbent and a given operating temperature, the diffusivities are set, and one of the means for improving the mass transfer consists in reducing the diameter of the crystals. A gain in global mass transfer will thus be obtained by reducing the size of the crystals.

A person skilled in the art will thus seek to minimize the diameter of the zeolite crystals as much as possible in order to improve the mass transfer.

Patent CN 1 267 185 thus claims adsorbents containing 90% to 95% of zeolite BaX or BaXK for the separation of para-xylene, in which the zeolite X crystals are between 0.1 μm and 0.4 μm in size, so as to improve the mass transfer performance. Similarly, application US 2009/0326308 describes a process for separating xylene isomers, the performance of which was improved by using adsorbents based on zeolite X crystals less than 0.5 μm in size.

The Applicant has nevertheless observed that the synthesis, filtration, handling and agglomeration of zeolite crystals whose size is less than 0.5 μm involve burdensome, uneconomical processes which are thus difficult to render industrializable.

Furthermore, such adsorbents comprising crystals less than 0.5 μm in size also prove to be more fragile, and it then becomes necessary to increase the content of agglomeration binder in order to reinforce the cohesion of the crystals with each other in the adsorbent. However, increasing the content of agglomeration binder leads to densification of the adsorbents, which causes an increase in the macropore diffusional resistance. Thus, despite reduced intra-crystalline diffusional resistance due to the decrease in the size of the crystals, the increase in macropore diffusional resistance on account of the densification of the adsorbent does not allow an improvement in the overall transfer. Moreover, increasing the binder content does not make it possible to obtain a good adsorption capacity.

It thus appears difficult to obtain adsorbents with all the following properties combined:

- the fastest possible mass transfer within the adsorbent, i.e. the lowest possible and ideally virtually zero resistance to mass transfer,
- high adsorption selectivity properties for para-xylene with respect to the other C8 aromatic molecules to ensure efficient separation,
- the largest possible adsorption capacity (i.e. the largest possible content of zeolite (active crystalline phase in the sense of adsorption)),
- an optimum mechanical crushing strength.

BRIEF SUMMARY OF THE INVENTION

The Applicant has developed a zeolite-based adsorbent which has a compromise between maximal para-xylene adsorption selectivity, maximal adsorption capacity and minimal resistance to mass transfer, i.e. the fastest possible transportation of molecules within the adsorbent.

The Applicant has also developed a process for preparing said adsorbents, and in particular a process for preparing said adsorbents that is more economical than the processes described in the prior art that might lead to said adsorbents. The adsorbents according to the present invention prove to be particularly effective for separating gaseous or liquid mixtures of isomers, more particularly xylenes and especially for separating very pure para-xylene from an aromatic hydrocarbon feedstock containing isomers containing 8 carbon atoms.

In the text hereinbelow, and unless otherwise indicated, the limits of a range of values are included in that range, especially in the expressions "between . . . and . . . " and "from . . . to . . . ".

BRIEF DESCRIPTION OF THE DRAWING

The figure illustrates the pore diameter distribution curves determined from the analysis by mercury intrusion performed on the adsorbents of Examples 2 to 4.

DETAILED DESCRIPTION

Adsorbent According to the Invention

Thus, and according to a first subject, the present invention relates to an adsorbent comprising a zeolite-based phase and a non-zeolite-based phase, said adsorbent having:

- an outer surface area of less than or equal to 30 $m^2 \cdot g^{-1}$, preferably less than or equal to 20 $m^2 \cdot g^{-1}$,
- a zeolite-based phase comprising at least one zeolite of FAU structure of X type,
- and a pore diameter distribution, determined by mercury intrusion according to standard ASTM D 4284-83 and expressed by the volume distribution dV/d log $D_{Hg}$, in which $D_{Hg}$ is the apparent pore diameter and V is the pore volume, the mode of which is between 100 nm and 250 nm, limits inclusive.

According to a preferred embodiment, the pore diameter distribution of the adsorbent corresponds to a unimodal distribution.

The term "unimodal distribution" means a distribution having a single peak. A unimodal diameter distribution is thus characterized by a single peak, for which the value of the diameter at the top of the peak is known as the "mode" or the "dominant value" and represents the most frequent value of the distribution. When a distribution has two peaks separated by a trough, the distribution is said to be bimodal.

The invention does not relate to the case of bimodal or even multimodal distributions, i.e. distributions in which there are several zones of concentration of values separated by discontinuities. Such distributions are characteristic of the presence of several populations of pores of different diameters.

Advantageously, the micropore volume of the adsorbent according to the invention, evaluated by the t-plot method from the nitrogen ($N_2$) adsorption isotherm at a temperature of 77 K, is greater than 0.200 $cm^3 \cdot g^{-1}$. Said nitrogen adsorption isotherm is measured, after degassing under vacuum ($P<6.7\times10^{-4}$ Pa), at a temperature of between 300° C. and 450° C. for a time ranging from 9 hours to 16 hours, preferably at 400° C. for 10 hours.

Advantageously, the adsorbent according to the present invention comprises a non-zeolite-based phase in a content of between 2% and 8% by weight relative to the total weight of the adsorbent. According to another preferred embodiment of the invention, the adsorbent comprises barium, or barium and potassium.

The outer surface area of the zeolite-based adsorbent of the invention is calculated via the t-plot method from the nitrogen adsorption isotherm at a temperature of 77 K, after degassing under vacuum ($P<6.7\times10^{-4}$ Pa), at a temperature of between 300° C. and 450° C. for a time ranging from 9 hours to 16 hours, preferably at 400° C. for 10 hours. The outer surface area of the FAU zeolite crystals used in the agglomeration is measured in the same manner. The outer surface area represents a part of the BET surface area which calculates the total porous surface in $m^2$/g (S BET=microporous surface area+outer surface area).

According to a preferred aspect, the barium (Ba) content of the zeolite-based adsorbent of the invention, expressed as barium oxide (BaO), is greater than 10%, preferably greater than 15%, very preferably greater than 20%, even more preferably greater than 23%, or even greater than 33%, by weight relative to the total weight of the adsorbent, and, advantageously, the barium content is between 23% and 42%, and typically between 30% and 40%, limits inclusive, by weight relative to the total weight of the adsorbent.

According to another preferred aspect, the potassium (K) content of the zeolite-based adsorbent of the invention, expressed as potassium oxide ($K_2O$), is less than 25%, preferably between 0 and 20%, even more preferably between 0 and 15% and very preferably from 0 to 10%, limits inclusive, by weight relative to the total weight of the adsorbent.

According to yet another preferred embodiment, the total content of alkali metal or alkaline-earth metal ions, other than barium and potassium, expressed as the total content of alkali metal or alkaline-earth metal ion oxides, other than barium oxide BaO and potassium oxide $K_2O$, is between 0 and 5%, limits inclusive, relative to the total weight of the adsorbent.

Advantageously, the zeolite-based adsorbent according to the invention has a total volume contained in the macropores and mesopores (sum of the macropore volume and the mesopore volume) measured by mercury intrusion according to standard ASTM D 4284-83, of between 0.15 $cm^3 \cdot g^{-1}$ and 0.5 $cm^3 \cdot g^{-1}$, preferably between 0.20 $cm^3 \cdot g^{-1}$ and 0.40 $cm^3 \cdot g^{-1}$ and very preferably between 0.20 $cm^3 \cdot g^{-1}$ and 0.35 $cm^3 \cdot g^{-1}$, all these ranges of values being understood as inclusive of the limits.

According to a preferred embodiment of the present invention, the zeolite-based adsorbent comprises macropores, mesopores and also micropores. The term "macropores" means pores whose diameter is strictly greater than 50 nm. The term "mesopores" means pores whose diameter is between 2 nm and 50 nm, limits inclusive. The term "micropores" means pores whose diameter is less than 2 nm.

In addition, the adsorbent of the invention advantageously has a (macropore volume)/(macropore volume+mesopore volume) ratio of between 0.2 and 1 and very preferably between 0.6 and 1, limits inclusive.

In the context of the present invention, a zeolite-based adsorbent whose micropore volume, evaluated via the t-plot method from the nitrogen ($N_2$) adsorption isotherm at a temperature of 77 K, is greater than 0.200 $cm^3 \cdot g^{-1}$, preferably between 0.205 $cm^3 \cdot g^{-1}$ and 0.300 $cm^3 \cdot g^{-1}$ and more preferably between 0.205 $cm^3 \cdot g^{-1}$ and 0.290 $cm^3 \cdot g^{-1}$, is also preferred.

In the context of the present invention, the mechanical strength is measured by the Shell method series SMS 1471-74 adapted for agglomerates less than 1.6 mm in size. This mechanical strength, measured for the zeolite-based adsorbent defined previously, is generally between 1.5 MPa and 4 MPa, preferably between 1.7 MPa and 4 MPa, more preferably between 1.8 MPa and 4 MPa and most preferably between 2 MPa and 4 MPa, limits inclusive.

According to yet another preferred embodiment, the zeolite-based adsorbent according to the invention has an Si/Al atomic ratio of between 1.00 and 1.50, limits inclusive, preferably between 1.05 and 1.50, limits inclusive, and more preferably between 1.15 and 1.50, limits inclusive.

Among the zeolites of FAU structure and of X type, it is now commonly accepted to recognize, inter alia, two subgroups known as LSX zeolites and MSX zeolites. LSX zeolites have an Si/Al atomic ratio of about 1 and MSX zeolites have an Si/Al atomic ratio of between about 1.05 and about 1.15, limits inclusive. According to a preferred embodiment, the at least one FAU zeolite is a zeolite X with an Si/Al atomic ratio of between 1.15 and 1.50, limits inclusive. According to another preferred embodiment, the at least one zeolite X is a zeolite of LSX type with an Si/Al atomic ratio equal to about 1.

In the zeolite-based adsorbent of the present invention, and according to a preferred embodiment, the term "FAU zeolite of X type" means the FAU zeolites of X type defined above, these said zeolites being hierarchically porous, i.e. hierarchically porous zeolites of X type (or HPX zeolite), hierarchically porous zeolites of MSX type (or HPMSX) and hierarchically porous zeolites of LSX type (or HPLSX), and more particularly hierarchically porous FAU zeolites with an Si/Al atomic ratio of between 1.00 and 1.50, limits inclusive, preferably between 1.05 and 1.50, more preferably between 1.05 and 1.40, limits inclusive, and even more preferably between 1.15 and 1.40, limits inclusive.

The invention also comprises zeolite-based adsorbents comprising mixtures of two or more hierarchically porous FAU zeolites as have just been defined.

The term "hierarchically porous zeolite" means a zeolite bearing both micropores and mesopores, in other words a zeolite that is both microporous and mesoporous. The term "mesoporous zeolite" means a zeolite whose microporous zeolite-based crystals have, together with the microporosity, internal cavities of nanometric size (mesoporosity), which are readily identifiable by observation using a transmission electron microscope (TEM), as described, for example, in U.S. Pat. No. 7,785,563: observation by transmission electron microscopy (TEM) makes it possible to check whether the zeolite-based crystals are filled (i.e. non-mesoporous) zeolite crystals or aggregates of filled zeolite crystals or mesoporous crystals or aggregates of mesoporous crystals.

The crystalline structure of the FAU zeolite of X type in the zeolite-based adsorbent of the present invention is identifiable by x-ray diffraction (known to those skilled in the art by the abbreviation XRD).

According to another preferred embodiment, no zeolite-based structure other than the FAU structure, preferably no zeolite-based structure other than the faujasite X structure, is detected by x-ray diffraction in the zeolite-based adsorbent of the present invention.

The expression "no zeolite-based structure other than the FAU structure" means less than 5% by weight, limits inclusive, and preferably less than 2% by weight, limits inclusive, of one or more zeolite-based phases other than the FAU structure. The mass fraction determined by XRD (technique described below) is expressed relative to the total weight of the adsorbent.

The non-zeolite-based phase (NZP) comprises, inter alia, an agglomeration binder used in the preparation method for ensuring the cohesion of the crystals with each other, whence the term "agglomerate" or "zeolite-based agglomerate" occasionally used instead of the term "zeolite-based adsorbent" of the invention, as described previously.

In the present invention, the term "binder" means an agglomeration binder which ensures the cohesion of the zeolite crystals in the zeolite-based adsorbent (or agglomerated zeolite-based material) of the invention. This binder also differs from the zeolite crystals in that it does not have a zeolite-based crystalline structure after calcination, for which reason the binder is often termed inert, and more precisely inert with respect to adsorption and ion exchange.

According to yet another preferred embodiment, the mass fraction of FAU zeolite, the FAU zeolite preferably being a zeolite of X type, is greater than or equal to 85% and preferably greater than or equal to 90% relative to the total weight of adsorbent of the present invention, the remainder to 100% preferably consisting of non-zeolite-based phase (NZP). According to a particularly advantageous aspect, the mass fraction of FAU zeolite is between 92% and 98% and preferably between 94% and 98% by weight, limits inclusive, relative to the total weight of the adsorbent of the present invention, the remainder to 100% preferably consisting of non-zeolite-based phase.

As already indicated, the mass fraction of zeolite(s) (degree of crystallinity) of the adsorbent according to the invention may be determined by x-ray diffraction analysis, known to those skilled in the art by the abbreviation XRD.

According to a preferred embodiment, the zeolite-based adsorbent according to the invention has a loss on ignition, measured at 950° C. according to standard NF EN 196-2, of less than or equal to 7.7%, preferably between 0 and 7.7%, preferably between 3.0% and 7.7%, more preferably between 3.5% and 6.5% and advantageously between 4.5% and 6.0%, limits inclusive.

Unless otherwise indicated in the present description, the indicated proportions are weight proportions, counted for the solid constituents as calcined equivalents, on the basis of calcination performed at 950° C. for 1 hour.

Process for Preparing the Adsorbent According to the Invention

Another subject of the invention relates to a process for preparing the zeolite-based adsorbent according to the invention, said process comprising at least the steps of:

a) agglomeration of crystals of at least one FAU zeolite, preferably FAU structure of X type zeolite, with an outer surface area, measured by the nitrogen adsorption, of greater than 20 $m^2 \cdot g^{-1}$, preferably between 20 $m^2 \cdot g^{-1}$ and 200 $m^2 \cdot g^{-1}$, limits inclusive, more preferably between 40 $m^2 \cdot g^{-1}$ and 150 $m^2 \cdot g^{-1}$, limits inclusive, with a binder preferably comprising at least 80% of clay or of a mixture of clays and with up to 5% of additives and also with the amount of water which allows the forming of the agglomerated material, followed by drying and calcination of the agglomerates;

b) zeolitization of all or part of the binder by placing the agglomerates obtained in step a) in contact with an aqueous basic solution, optionally in the presence of at least one structuring agent;

c) optional removal of the structuring agent optionally present;

d) cationic exchange(s) of the agglomerates of step b) or c) by placing in contact with a solution of barium ions or of barium ions and potassium ions;

e) optional additional cationic exchange of the agglomerates of step d) by placing in contact with a solution of potassium ions;

f) washing and drying of the agglomerates obtained in step d) or e), at a temperature of between 50° C. and 150° C.; and g) production of the zeolite-based adsorbent according to the invention by activation of the agglomerates obtained in step f) under a stream of oxidizing and/or inert gas, especially with gases such as oxygen, nitrogen, air, a dry and/or decarbonated air, or an oxygen-depleted air, which is optionally dry and/or decarbonated, at a temperature of between 100° C. and 400° C., preferably between 200° C. and 300° C.

In a preferred embodiment of the process for preparing the zeolite-based adsorbent of the present invention, the drying of the agglomerates in step a) above is generally performed at a temperature of between 50° C. and 150° C., and the calcination of the dried agglomerates is generally performed under a stream of oxidizing and/or inert gas, especially with gases such as oxygen, nitrogen, air, a dry and/or decarbonated air, or an oxygen-depleted air, which is optionally dry and/or decarbonated, at a temperature above 150° C., typically between 180° C. and 800° C., preferentially between 200° C. and 650° C., for a few hours, for example from 2 hours to 6 hours.

According to one embodiment of the present invention, the FAU zeolite crystals used during the agglomeration step (step a) have a number-mean diameter of between 1 μm and 20 μm, limits inclusive, more preferably between 1.5 μm and 20 μm, limits inclusive, more preferentially between 1.8 μm and 10 μm, limits inclusive, better still between 2 μm and 10 μm, limits inclusive, and more preferably between 2 μm and 8 μm, limits inclusive.

In the present document, the term "number-mean diameter" or "size" is used without preference, in particular for the zeolite crystals. The method for measuring these magnitudes is explained later in the description.

According to a preferred embodiment, the zeolite of FAU structure is as defined and advantageously has an Si/Al atomic ratio preferably between 1.00 and 1.50, preferably between 1.05 and 1.50, more preferably between 1.05 and 1.40, more preferably between 1.10 and 1.40 and even more preferably between 1.15 and 1.40, limits inclusive.

As indicated previously, the outer surface area of the crystals used in step a) of the process described above is calculated via the t-plot method from the nitrogen adsorption isotherm at a temperature of 77 K, after degassing under vacuum ($P<6.7\times10^{-1}$ Pa), at a temperature of between 300° C. and 450° C. for a time ranging from 9 hours to 16 hours, preferably at 400° C. for 10 hours.

According to a preferred embodiment, the FAU zeolite used in step a) is a hierarchically porous FAU zeolite. Crystals of hierarchically porous FAU zeolite having a high outer surface area may be obtained according to various methods known to those skilled in the art, for example according to the synthesis described by lnayat et al. (*Angew. Chem. Int. Ed.*, (2012), 51, 1962-1965).

It is also possible to prepare said crystals by synthesis by seeding and/or by adjusting the synthetic operating conditions such as the $SiO_2/Al_2O_3$ ratio, the sodium content and the alkalinity of the synthetic mixture or alternatively according to conventional processes of post-treatment of FAU zeolite crystals known to those skilled in the art.

The post-treatment processes generally consist in removing atoms from the already-formed zeolite network, either by one or more acidic treatments which dealuminate the solid, these treatments being followed by one or more washes with sodium hydroxide (NaOH) so as to remove the aluminium-based residues formed, as described, for example, by D. Verboekend et al. (*Adv. Funct. Mater.,* 22, (2012), pp. 916-928), or alternatively by treatments which combine the action of an acid and that of a structuring agent which improve the efficacy of the acidic treatment, as described, for example, in application WO2013/106816.

The processes for the direct synthesis of these zeolites (i.e. synthetic processes other than the post-treatment) are preferred and generally involve one or more structuring agents or sacrificial templates.

The sacrificial templates that may be used may be of any type known to those skilled in the art and especially those described in application WO 2007/043731. According to a preferred embodiment, the sacrificial template is advantageously chosen from organosilanes and more preferentially from [3-(trimethoxysilyl)propyl]octadecyldimethylammonium chloride, [3-(trimethoxysilyl)propyl]hexadecyldimethylammonium chloride, [3-(trimethoxysilyl)propyl]dodecyldimethylammonium chloride, [3-(trimethoxysilyl)propyl]octylammonium chloride, N-[3-(trimethoxysilyl)propyl]aniline, 3-[2-(2-aminoethylamino)ethylamino]propyltrimethoxysilane, N-[3-(trimetho-xysilyl)propyl]-N'-(4-vinylbenzyl)ethylenediamine, triethoxy-3-(2-imidazolin-1-yl)propyl-silane, 1-[3-(trimethoxysilyl)propyl]urea, N-[3-(trimethoxysilyl)propyl]ethylenediamine, [3-(diethylamino)propyl]trimethoxysilane, (3-glycidyloxypropyl)trimethoxysilane, 3-(trimethoxysilyl)propyl methacrylate, [2-(cyclohexenyl)ethyl]triethoxysilane, dodecyltriethoxysilane, hexadecyltrimethoxysilane, (3-aminopropyl)trimethoxysilane, (3-mercaptopropyl)trimethoxysilane and (3-chloropropyl)trimethoxysilane, and also mixtures of two or more thereof in all proportions.

Among the sacrificial templates listed above, [3-(trimethoxysilyl)propyl]octadecyldimethylammonium chloride, or TPOAC, is most particularly preferred.

Use may also be made of sacrificial templates of higher molar mass, for example PPDA (Polymer Poly-DiallyldimethylAmmonium), PVB (PolyVinyl Butyral) and other oligomeric compounds known in the field for increasing the diameter of the mesopores.

According to a preferred embodiment of the process of the present invention, agglomeration of crystals of at least one hierarchically porous FAU zeolite, as described previously, prepared in the presence of a sacrificial template intended to be removed, is performed in step a).

This removal may be performed according to the methods known to those skilled in the art, for example by calcination, and, in a non-limiting manner, the calcination of the zeolite crystals comprising the sacrificial template may be performed under a stream of an oxidizing and/or inert gas, especially with gases such as oxygen, nitrogen, air, a dry and/or decarbonated air, or an oxygen-depleted air, which is optionally dry and/or decarbonated, at one or more temperatures above 150° C., typically between 180° C. and 800° C., preferentially between 200° C. and 650° C., for a few hours, for example between 2 and 6 hours. The nature of the gases, the temperature increase ramps and the successive temperature stages and their durations will be adapted as a function of the nature of the sacrificial template.

The additional step of removal of the optional sacrificial template may be performed at any moment in the course of the process for preparing the zeolite-based adsorbent of the invention. The removal of said sacrificial template may thus advantageously be performed by calcination of the zeolite crystals before the agglomeration step a), or alternatively, concomitantly with the calcination of the adsorbent during step a).

However, it would not constitute a departure from the scope of the invention if the agglomeration of step a) comprised the agglomeration of several hierarchically porous FAU zeolites obtained according to different methods.

The synthesis of zeolite of FAU type generally takes place in sodic medium (sodium hydroxide and thus $Na^+$ cation). The crystals of FAU zeolite thus obtained predominantly, or even exclusively, comprise sodium cations. However, it would not constitute a departure from the scope of the invention to use crystals which have undergone one or more cationic exchanges, between the synthesis in Na form, before or after the optional removal of the sacrificial template if this step is carried out before performing step a). In this case, step d) and optionally the exchange step e) consequently become optionally unnecessary.

The size of the crystals of FAU zeolite used in step a) and of the crystals of FAU zeolite in the adsorbents according to the invention is measured by observation with a scanning electron microscope (SEM).

The agglomeration and forming (step a) may be performed according to any technique known to those skilled in the art, and in particular according to one or more of the techniques chosen from extrusion, compacting, agglomeration on a granulating plate, granulating drum, atomization and the like.

The proportions of agglomeration binder (see definition later) and of zeolite used are 8 parts to 15 parts by weight of binder for 92 parts to 85 parts by weight of zeolite.

After step a), the finest agglomerated adsorbents may be removed by cycloning and/or screening and/or the excessively coarse agglomerates may be removed by screening or crushing, in the case of extrudates, for example. The adsorbents thus obtained, whether in the form of beads, extrudates or the like, preferably have a volume-mean diameter, or their length (longest dimension when they are not spherical), of between 0.2 mm and 2 mm, in particular between 0.2 mm and 0.8 mm and preferably between 0.40 mm and 0.65 mm, limits inclusive.

The binder that may be used in the context of the present invention may thus be chosen from the conventional binders known to those skilled in the art, and preferably chosen from clays and mixtures of clays.

The clays are preferably chosen from kaolins, kaolinites, nacrites, dickites, halloysites, attapulgites, sepiolites, montmorillonites, bentonites, illites and metakaolins, and also mixtures of two or more thereof in all proportions.

Preferably, the agglomeration binder used in step a) contains at least one zeolitizable clay, preferably chosen from the family of kaolins, kaolinites, nacrites, dickites, halloysites and metakaolins, and mixtures thereof. Kaolin is preferred and most commonly used. The agglomeration binder used in step a) may also contain other mineral binders such as bentonite, attapulgite and the like. The term "zeolitizable clay" means a clay or a mixture of clays that are capable of being zeolitically converted, usually via the action of an aqueous basic solution.

Among the additives optionally used in step a), there may be a source of silica of any type known to a person skilled in the art, who is a specialist in zeolite synthesis, for example colloidal silica, diatomaceous earth, perlite, fly ash, sand, or any other form of solid silica.

During step a), besides the zeolite crystal(s), the binder may also comprise one or more additives. The additives are preferentially organic, for example lignin, starch, carboxymethylcellulose, surfactant molecules (cationic, anionic, nonionic or amphoteric), which are intended to facilitate the manipulation of the zeolite/clay paste by modification of the rheology and/or of the adhesive power or to give the final adsorbents satisfactory properties, especially in terms of macroporosity.

Mention may preferentially be made, but in a non-exhaustive manner, of methylcelluloses and derivatives thereof, lignosulfonates, polycarboxylic acids and carboxylic acid copolymers, amine derivatives thereof and salts thereof, especially alkaline salts and ammonium salts. The additives are introduced in a proportion of from 0 to 5% and preferably from 0.1% to 2% by weight relative to the total weight of the adsorbent.

SEM observation of the zeolite-based adsorbent makes it possible to confirm the presence of a non-zeolite-based phase comprising, for example, agglomeration binder or any other amorphous phase in the adsorbents.

For the calcination included in step a), the nature of the gases, the temperature increase ramps and the successive temperature stages, and also the respective durations thereof, will be adapted especially as a function of the nature of the sacrificial template to be removed and as a function of the nature of the binder used in the agglomeration step a).

Similarly, the zeolitization step b) is a step that is now well known to those skilled in the art, which may be performed according to any method described in the prior art, the alkaline aqueous solution used possibly being an aqueous solution of sodium or potassium hydroxide, the use of sodium hydroxide being most particularly preferred. As a general rule, the concentration of the alkaline zeolitization solution is between 0.5 M and 5 M.

The zeolitization is preferably performed with heating, at a temperature above room temperature, for example between room temperature (about 20° C.) and the boiling point of the alkaline zeolitization solution, for example at temperatures of the order of 80° C. to 100° C. The duration of the zeolitization process is generally between a few tens of minutes and a few hours, usually between about 1 hour and 8 hours.

According to one embodiment of the process of the present invention, step b) of zeolitization of at least part of the agglomeration binder may be performed in the presence of at least one structuring agent or sacrificial template intended to be removed according to the methods known to those skilled in the art, for example by calcination, the presence of the structuring agent having the purpose of creating a certain level of mesoporosity in the agglomerate of the invention so as to obtain a mesoporous zeolite-based agglomerate.

The nature of the structuring agent or sacrificial template may be of any type known to those skilled in the art and in particular chosen from those described above for the synthesis of hierarchically porous zeolite.

The amount of structuring agent, when it is present in the zeolitization step, may vary within wide proportions according to the desired degree of mesoporosity, and is advantageously between 0.1% and 50%, preferably between 0.1% and 33%, more preferably between 1% and 30% and advantageously between 5% and 30% by weight relative to the weight of clay(s).

Step c) of optional removal of the structuring agent, optionally introduced during the zeolitization step b) and intended to convert part of the agglomeration binder into mesoporous zeolite, may be performed via any means known to those skilled in the art and in particular by heat treatment, generally at a temperature above 150° C., typically between 180° C. and 650° C., preferentially between 200° C. and 600° C. In this case, the activation step g) performed at high temperature also allows the removal of the structuring agent, thus advantageously making it possible to dispense with step e) of removal of said structuring agent which will in fact be removed during the activation in step g).

The cationic exchange steps d) and e) described above are performed according to the standard methods known to those skilled in the art, and usually by placing the adsorbents obtained from step a) in contact with a barium salt, such as barium chloride ($BaCl_2$) and/or a potassium salt (KCl) and/or a barium and potassium salt, in aqueous solution at a temperature between room temperature and 100° C., and preferably between 80° C. and 100° C. so as rapidly to obtain high barium contents, i.e. contents preferably greater than 10%, preferably greater than 15%, very preferably greater than 20% and even more preferably greater than 23%, or even greater than 33%, expressed as weight of barium oxide relative to the total mass of the adsorbent.

Advantageously, the barium content expressed as barium oxide is between 23% and 42% and typically between 30% and 40%, limits inclusive, by weight relative to the total weight of the adsorbent. It is preferred to work with a large excess of barium ions relative to the cations of the zeolite that it is desired to exchange, typically an excess of the order of 10 to 12, advantageously by performing successive exchanges.

An optional potassium exchange in step e) may be performed before and/or after the barium exchange (step b). It is also possible in step a) to agglomerate crystals of FAU zeolite already containing barium or potassium ions or barium and potassium ions (pre-exchange of the cations present in the starting zeolite of FAU type, typically sodium cations, with barium or potassium ions or barium and potassium ions before step a) and to dispense with (or not) steps d) and/or e).

The Applicant has observed, surprisingly, that the cationic exchange step, which may be difficult on account of the relative fragility of the structure of the hierarchically porous zeolite crystals, does not affect the intrinsic properties of outer surface area and of micropore volume (related to the mass of the adsorbent once exchanged) of said hierarchically porous zeolite crystals.

After the cationic exchange step(s), washing is then performed, generally and preferably with water, followed by drying of the adsorbent thus obtained. The activation that follows the drying is performed conventionally, according to the methods known to those skilled in the art, for example at a temperature generally between 100° C. and 400° C., preferably between 200° C. and 300° C. The activation is performed for a time determined as a function of the desired loss on ignition. This time is generally between a few minutes and a few hours, typically from 1 to 6 hours.

Use of the Adsorbents According to the Invention

The present invention also relates to the uses of the zeolite-based adsorbents described above as adsorption agents advantageously capable of replacing the adsorption agents described in the literature, based on conventional crystals of zeolite of FAU type, and especially in the uses listed below:

- separation of C8 aromatic isomer fractions and especially of xylenes,
- separation of substituted toluene isomers such as nitrotoluene, diethyltoluene, toluenediamine, and the like,
- separation of cresols,
- separation of polyhydric alcohols, such as sugars.

According to another subject, the present invention relates to a process for the gas-phase or liquid-phase separation of xylene isomers using at least one zeolite-based adsorbent as defined previously.

The invention especially relates to a process for separating para-xylene from a feedstock to be treated of aromatic isomer fractions containing 8 carbon atoms, using, as para-xylene adsorption agent, a zeolite-based adsorbent as defined previously.

The desired product (para-xylene) may thus be separated out by preparative adsorption liquid chromatography (in batch mode), and advantageously in continuous mode in a simulated moving bed unit, i.e. with simulated counter-current or simulated co-current, and more particularly with simulated counter-current.

The operating conditions of an industrial simulated moving bed adsorption unit, functioning in counter-current mode, are generally the following:

- number of beds: 4 to 24,
- number of zones: at least 4 operating zones, each being located between a feed point (stream of feedstock to be treated or stream of desorbent) and a withdrawal point (stream of raffinate or stream of extract);
- temperature of between 100° C. and 250° C., preferably between 140° C. and 190° C.;
- pressure of the industrial unit between the bubble pressure of xylenes (or of toluene when toluene is chosen as desorbent) at the process temperature and 3 MPa;
- ratio of the desorbent/feedstock flow rates between 0.7 and 2.5, preferably between 0.7 and 2.0, for example between 0.9 and 1.8 for a stand-alone adsorption unit, and between 0.7 and 1.4 for an adsorption unit combined with a crystallization unit,
- recycling rate between 2 and 12 and preferably between 2.5 and 6,
- cycle time, corresponding to the time between two injections of desorbent onto a given bed: advantageously between 4 and 25 minutes.

Reference may be made in this respect to the teaching of patents U.S. Pat. Nos. 2,985,589, 5,284,992 and 5,629,467.

The operating conditions of an industrial simulated co-current adsorption unit are generally the same as those operating in simulated counter-current mode with the exception of the recycling rate, which is generally between 0.8 and 7. Reference may be made in this respect to patents U.S. Pat. Nos. 4,402,832 and 4,498,991.

The desorbent is a desorption solvent whose boiling point is less than that of the feedstock, such as toluene, or higher than that of the feedstock, such as para-diethylbenzene (PDEB). Advantageously, the desorbent is toluene or para-diethylbenzene.

The selectivity of the adsorbents according to the invention for the adsorption of the para-xylene contained in C8 aromatic fractions is optimal when the loss on ignition thereof measured at 950° C. is preferably less than or equal to 7.7%, preferably between 0 and 7.7%, very preferably between 3.0% and 7.7%, more preferably between 3.5% and 6.5% and even more preferably between 4.5% and 6%, limits inclusive.

The water content in the inlet streams constituted by the feedstock and/or desorbent streams is preferentially adjusted to between 20 ppm and 150 ppm, for example by adding water to the feedstock and/or desorbent streams.

The zeolite-based adsorbents of the invention have improved mass transfer properties while at the same time maintaining optimum properties of selectivity for para-xylene, a maximum adsorption capacity, and while conserving high mechanical strength for use in a process for the liquid-phase separation of para-xylene, preferably of simulated counter-current type.

It has been most particularly observed that the zeolite-based adsorbents according to the present invention have a combined index CI of greater than 14 and in general greater than 15, which is entirely noteworthy relative to the CI values observed with the adsorbents of the prior art.

The CI index is defined by the following formula:

$$CI = \frac{\text{selectivity} \times \text{capacity}}{EHTP}$$

in which

- the "selectivity" parameter represents the selectivity between para-xylene and meta-xylene,
- the "capacity" parameter represents the xylene adsorption capacity expressed in % ($cm^3$ of $C_8$-aromatics adsorbed per $cm^3$ of column)
- the "EHTP" parameter represents the equivalent height of theoretical plates measured on para-xylene relative to the column length (expressed in %).

The various parameters are determined by the breakthrough technique in the liquid phase in a test performed under the following conditions:

- the adsorption temperature is 175° C.,
- the surface velocity (flow rate/column cross section) of circulation of the liquid at the test temperature is 1.3 $cm \cdot s^{-1}$,
- the desorption solvent used is para-diethylbenzene,
- composition of the feedstock is as follows:
  - para-xylene: 45% by weight
  - meta-xylene: 45% by weight
  - isooctane: 10% by weight (this is used as a tracer for estimating the non-selective volumes and does not participate in the separation).

According to yet another aspect, the present invention relates to the use of at least one zeolite-based adsorbent with a combined index CI of greater than 14 and preferably greater than 15, in processes for the gas-phase or liquid-phase separation of xylene isomers, such as those defined previously.

In this use, said at least one zeolite-based adsorbent has a mechanical strength advantageously greater than 1.5 MPa, preferably between 1.7 MPa and 4 MPa, more preferably between 1.8 MPa and 4 MPa and most preferably between 2 MPa and 4 MPa, limits inclusive. In the context of the present invention, the mechanical strength is measured via the Shell method series SMS 1471-74 adapted for agglomerates less than 1.6 mm in size.

Characterization Techniques

Particle Size of the Zeolite-based Crystals

Estimation of the number-mean diameter of the FAU zeolite crystals used during the agglomeration step a) and of the crystals contained in the zeolite-based adsorbents according to the invention is performed by observation using a scanning electron microscope (SEM).

In order to estimate the size of the zeolite crystals on the samples, a set of images is taken at a magnification of at least 5000. The diameter of at least 200 crystals is then measured using dedicated software. The accuracy is of the order of 3%.

Chemical Analysis of the Zeolite-based Adsorbents—Si/Al Ratio and Degree of Exchange:

An elemental chemical analysis of the final product obtained after steps a) to e) described previously may be performed according to various analytical techniques known to those skilled in the art. Among these techniques, mention may be made of the technique of chemical analysis by x-ray fluorescence as described in standard NF EN ISO 12677: 2011 on a wavelength-dispersive spectrometer (WDXRF), for example the Tiger S8 machine from the company Brüker.

X-ray fluorescence is a non-destructive spectral technique which exploits the photoluminescence of atoms in the x-ray range, to establish the elemental composition of a sample. Excitation of the atoms, generally with an x-ray beam or by electron bombardment, generates specific radiations after returning to the ground state of the atom. The x-ray fluorescence spectrum has the advantage of depending very little on the chemical combination of the element, which offers a precise determination, both quantitatively and qualitatively. A measurement uncertainty of less than 0.4% by weight is conventionally obtained after calibration for each oxide.

These elemental chemical analyses make it possible to check both the Si/Al atomic ratio of the zeolite used during the preparation of the adsorbent, and also the Si/Al atomic ratio of the adsorbent and to check the quality of the ion exchange described in step c) and in the optional step d). In the description of the present invention, the measurement uncertainty of the Si/Al atomic ratio is ±5%.

The quality of the ionic exchange is linked to the number of moles of sodium oxide, $Na_2O$, remaining in the zeolite-based adsorbent after exchange. More precisely, the degree of exchange with barium ions is estimated by evaluating the ratio between the number of moles of barium oxide, BaO, and the number of moles of the combination ($BaO+Na_2O+K_2O$). Similarly, the degree of exchange with potassium ions is estimated by evaluating the ratio between the number of moles of potassium oxide, $K_2O$, and the number of moles of the combination ($BaO+K_2O+Na_2O$). It should be noted that the contents of the various oxides are given as weight percentages relative to the total weight of the anhydrous zeolite-based adsorbent.

Particle Size of the Zeolite-based Adsorbents:

The determination of the volume-mean diameter of the zeolite-based adsorbents obtained after step a) of agglomeration and of forming is performed by analysis of the particle size distribution of a sample of adsorbent by imaging according to standard ISO 13322-2:2006, using a conveyor belt for passing the sample before the objective lens of the camera.

The volume-mean diameter is then calculated from the particle size distribution by applying standard ISO 9276-2: 2001. In the present document, the term "volume-mean diameter" or "size" is used for the zeolite-based adsorbents. The accuracy is of the order of 0.01 mm for the size range of adsorbents of the invention.

Mechanical Strength of the Zeolite-based Adsorbents:

The crushing strength of a bed of zeolite-based adsorbents as described in the present invention is characterized according to the Shell method series SMS1471-74 (Shell Method Series SMS1471-74 *Determination of Bulk Crushing Strength of Catalysts. Compression-Sieve Method*), associated with the BCS Tester machine sold by the company Vinci Technologies. This method, initially intended for characterizing catalysts of 3 mm to 6 mm, is based on the use of a 425 μm screen, which will make it possible especially to separate the fines created during the crushing. The use of a 425 μm screen remains suitable for particles with a diameter of greater than 1.6 mm, but should be adapted according to the particle size of the adsorbents that it is desired to characterize.

The adsorbents of the present invention, generally in the form of beads or extrudates, generally have a volume-mean diameter or a length i.e. longest dimension in the case of non-spherical adsorbents, of between 0.2 mm and 2 mm, in particular between 0.2 mm and 0.8 mm and preferably between 0.40 mm and 0.65 mm, limits inclusive. Consequently, a 100 μm screen is used instead of the 425 μm screen mentioned in the Shell method standard SMS 1471-74.

Measuring protocol is as follows: a sample of 20 $cm^3$ of agglomerated adsorbents, prescreened with the appropriate screen (100 μm) and predried in an oven for at least 2 hours at 250° C. (instead of 300° C. mentioned in the Shell method standard SMS 1471-74), is placed in a metal cylinder of known internal cross section. An increasing force is imposed in stages on this sample by means of a piston, through a bed of 5 $cm^3$ of steel beads so as better to spread the force exerted by the piston on the agglomerated adsorbents (use of beads 2 mm in diameter for particles of spherical shape with a diameter strictly less than 1.6 mm). The fines obtained at the various pressure stages are separated out by screening (suitable screen of 100 μm) and weighed.

The bulk crushing strength is determined by the pressure in megapascals (MPa) for which the amount of cumulative fines passing through the screen rises to 0.5% by weight of the sample. This value is obtained by plotting on a graph the mass of fines obtained as a function of the force applied to the bed of adsorbent and by interpolating to 0.5% by mass of cumulative fines. The mechanical bulk crushing strength is typically between a few hundred kPa and a few tens of MPa and generally between 0.3 MPa and 3.2 MPa. The accuracy is conventionally less than 0.1 MPa.

Non-zeolite-based Phase of the Zeolite-based Adsorbents:

The content of non-zeolite-based phase NZP, for example the content of agglomeration binder and of any other amorphous phase, is calculated according to the following equation:

$$NZP=100-\Sigma\ (ZP),$$

where ZP represents the sum of the amounts of zeolite X fractions within the meaning of the invention.

Mass Amount of the Zeolite-based Fractions of the Zeolite-based Adsorbents

Identification of the zeolite fractions contained in the adsorbent is performed by x-ray diffraction (XRD) analysis. This analysis is performed on a Brüker brand machine. Identification of the crystalline phases present in the zeolite-based adsorbent is performed by comparison with the ICDD database sheets. For example, the presence of type X zeolite exchanged with barium will be confirmed by comparison of the lines of the diffractogram obtained with ICDD sheet No. 38-0234 ("Zeolite X, (Ba)"). The mass amount of the zeolite-based fractions is evaluated from the peak intensities of the diffractograms, taking as reference the peak intensities of a suitable reference (zeolite of the same chemical nature assumed to be 100% crystalline under cationic treatment conditions identical to those of the adsorbent under consideration). The peaks, which make it possible to work back to the crystallinity, are the strongest peaks of the 2θ angular zone between 9° and 37°, namely the peaks observed in the 2θ angular ranges between 11° and 13°, between 22° and 26° and between 31° and 33°, respectively.

Micropore Volume and Outer Surface Area

The crystallinity of the crystals and of the zeolite-based adsorbents of the invention is also evaluated by measuring their micropore volume by comparing it with that of a suitable reference (zeolite that is 100% crystalline under identical cationic treatment conditions or theoretical zeolite). This micropore volume is determined from the measurement of the adsorption isotherm of a gas, such as nitrogen, at its liquefaction temperature.

Prior to the adsorption, the zeolite-based sample (whether it is an adsorbent or crystals) is degassed between 300° C. and 450° C. for a time of between 9 hours and 16 hours, under vacuum ($P < 6.7\times10^{-4}$ Pa). Measurement of the nitrogen adsorption isotherm at 77 K is then performed on a machine of ASAP 2020 M type from Micromeritics, taking at least 35 measurement points at relative pressures of ratio $P/P_0$ between 0.002 and 1.

The micropore volume and the outer surface area are determined from the isotherm obtained by the t-plot method, by applying standard ISO 15901-3: 2007 and by calculating the statistical thickness t via the Harkins-Jura equation. The micropore volume and the outer surface area are obtained by linear regression on the points of the t-plot between 0.45 nm and 0.57 nm, respectively from the y-axis to the origin and from the slope of the linear regression. The evaluated micropore volume is expressed in $cm^3$ of liquid adsorbate per gram of anhydrous adsorbent. The outer surface area is expressed in $m^2$ per gram of anhydrous adsorbent.

Macropore and Mesopore Volume, Pore Diameter Distribution by Mercury Intrusion, and Grain Density The macropore and mesopore volumes and the grain density are measured by mercury intrusion porosimetry. An Autopore® 9500 mercury porosimeter from Micromeritics is used for analysing the distribution of the pore volume contained in the macropores and in the mesopores.

The experimental method, described in the machine's operating manual which makes reference to standard ASTM D 4284-83, consists in placing a sample of adsorbent (zeolite-based granular material to be measured) (of known loss on ignition) weighed beforehand, into a porosimetry cell and then, after first degassing (evacuation pressure of 30 μmHg for at least 10 minutes), in filling the cell with mercury to a given pressure (0.0036 MPa) and then in applying a pressure increasing in stages up to 400 MPa in order gradually to make the mercury penetrate into the pore network of the sample. The pore volume increment dV into which the mercury penetrates at each pressure stage is recorded. The number of pressure stages is typically about 15 between 0.0036 MPa and 0.2 MPa, and about 90 between 0.2 MPa and 400 MPa.

The relationship between the applied pressure and the apparent pore diameter $D_{Hg}$ is established by assuming cylindrical pores, a contact angle between the mercury and the wall of the pores of 140° and a mercury surface tension of 485 dynes/cm. The cumulative amount of mercury introduced as a function of the applied pressure is recorded. The value from which the mercury fills all the inter-granular voids is set at 0.2 MPa, and it is considered that beyond this value, the mercury penetrates into the pores of the granular material. The grain volume (Vg) is then calculated by subtracting the cumulative volume of mercury at this pressure (0.2 MPa) from the volume of the porosimetry cell, and by dividing this difference by the mass of the anhydrous equivalent granular material, i.e. the mass of said material corrected for the loss on ignition.

The grain density is the inverse of the grain volume (Vg), and is expressed in grams of anhydrous adsorbent per $cm^3$.

The macropore volume of the granular material is defined as being the cumulative volume of mercury introduced at a pressure of between 0.2 MPa and 30 MPa, corresponding to the volume contained in the pores with an apparent diameter of greater than 50 nm. The mesopore volume of the granular material is defined as being the cumulative volume of mercury introduced at a pressure of between 30 MPa and 400 MPa.

In the present document, the macropore and mesopore volumes of the zeolite-based adsorbents, expressed in $cm^3 \cdot g^{-1}$, are thus measured by mercury intrusion and relative to the mass of the sample as anhydrous equivalent, i.e. the mass of said material corrected for the loss on ignition.

The pore diameter distribution determined by mercury intrusion is expressed by the volume distribution dV/d log $D_{Hg}$ represented as a function of the apparent pore diameter of the pores $D_{Hg}$. The dV/d log $D_{Hg}$ values are calculated from the pore volume increment dV into which the mercury penetrates at each pressure stage relative to the difference in corresponding apparent pore diameter.

Loss on Ignition of the Zeolite-based Adsorbents:

The loss on ignition is determined under an oxidizing atmosphere, by calcination of the sample in air at a temperature of 950° C.±25° C., as described in standard NF EN 196-2 (April 2006). The measurement standard deviation is less than 0.1%.

Characterization of the Liquid-phase Breakthrough Adsorption:

The technique used for characterizing the liquid-phase adsorption of molecules onto a porous solid is the technique known as breakthrough, described by Ruthven in *Principles of Adsorption and Adsorption Processes* (chapters 8 and 9, John Wiley & Sons, 1984), which defines the technique of breakthrough curves as the study of the response to the injection of a grade of adsorbable constituents. Analysis of the mean exit time (first moment) of the breakthrough curves gives information regarding the amounts adsorbed and also makes it possible to evaluate the selectivities, i.e. the separation factor, between two adsorbable constituents.

The injection of a non-adsorbable constituent used as tracer is recommended for the estimation of the non-selective volumes. Analysis of the dispersion (second moment) of the breakthrough curves makes it possible to evaluate the equivalent height of theoretical plates, based on the representation of a column by a finite number of ideally stirred hypothetical reactors (theoretical stages), which is a direct measurement of the axial dispersion and of the resistance to mass transfer of the system.

EXAMPLES

Example A

Synthesis of Hierarchically Porous FAU Zeolite

FAU zeolite with a high outer surface area is synthesized directly according to the article by Inayat et al. (*Angew. Chem. lnt. Ed.*, (2012), 51, 1962-1965).

Step 1): Preparation of the Growth Gel in the Reactor Stirred with Archimedean Screw at 300 rpm A growth gel is prepared in a stainless-steel reactor equipped with a heating jacket, a temperature probe and a stirrer, by mixing an aluminate solution containing 119 g of sodium hydroxide (NaOH), 128 g of alumina trihydrate ($Al_2O_3.3H_2O$, containing 65.2% by weight of $Al_2O_3$) and 195.5 g of water at 25° C. over 25 minutes, with a stirring speed of 300 rpm, with a silicate solution containing 565.3 g of sodium silicate, 55.3 g of NaOH and 1997.5 g of water at 25° C.

The stoichiometry of the growth gel is as follows: 3.48 $Na_2O/Al_2O_3/3.07\ SiO_2/180\ H_2O$. Homogenization of the growth gel is performed with stirring at 300 rpm for 25 minutes at 25° C.

Step 2): Introduction of the Structuring Agent into the Reaction Medium 27.3 g of a solution of TPOAC at 60% in MeOH are introduced into the reaction medium with a stirring speed of 300 rpm (TPOAC/$Al_2O_3$ mole ratio=0.04). After 5 minutes of homogenization, the stirring speed is lowered to 50 rpm.

Step 3): Maturation Phase

The reaction medium is kept stirring at 50 rpm at 25° C. for 22 hours, and crystallization is then started.

Step 4): Crystallization

The stirring speed is maintained at 50 rpm, and the reactor jacket is set to a nominal value of 80° C. so that the reaction medium rises in temperature to 75° C. over 80 minutes. After 72 hours at a stage of 75° C., the reaction medium is cooled by circulating cold water through the jacket to stop the crystallization.

Step 5): Filtration/Washing

The solids are recovered on a sinter and then washed with the permuted water to neutral pH.

Step 6): Drying/Calcination

In order to characterize the product, drying is performed in an oven at 90° C. for 8 hours, and the loss on ignition of the dried product is 22% by weight.

Calcination of the dried product, which is necessary to release both the microporosity (water) and the mesoporosity by removing the structuring agent, is performed with the following temperature profile: 30 minutes of increase to 200° C., then 1 hour at a stage of 200° C., then 3 hours of increase to 550° C., and finally 1.5 hours at a stage of 550° C.

The crystals obtained are identified by x-ray diffraction (XRD analysis) as being faujasite crystals. Chemical analysis of the solid gives an Si/Al atomic ratio=1.24. The number-mean diameter of the crystals of the mesoporous zeolite (or hierarchically porous zeolite) thus obtained is 4.5 µm.

The micropore volume and the outer surface area measured according to the t-plot method from the nitrogen adsorption isotherm at 77 K after degassing under vacuum at 400° C. for 10 hours are, respectively, 0.260 $cm^3 \cdot g^{-1}$ and 90 $m^2 \cdot g^{-1}$ expressed per gram of dry adsorbent.

Example B

Synthesis of Non-Mesoporous Zeolite X crystals with an Si/Al Atomic Ratio=1.25, a Number-Mean Diameter of 1.0 µm and an Na/Al Atomic Ratio =1

A gel of molar composition 3.5 $Na_2O$–2.8 $SiO_2$–$Al_2O_3$–130 $H_2O$ is prepared by mixing the following reagents: sodium silicate, sodium aluminate and water. The gel is matured at 35° C. for 20 hours, and crystallization is performed for 4 hours at 100° C.

The crystals obtained after filtration and washing are identified by x-ray diffraction (XRD analysis) as being faujasite crystals. Chemical analysis of the solid gives an Si/Al atomic ratio=1.25. The number-mean diameter of the zeolite crystals is 1.0 µm. The micropore volume and the outer surface area measured according to the t-plot method from the nitrogen adsorption isotherm at 77 K after degassing under vacuum at 400° C. for 10 hours are, respectively, 0.345 $cm^3 \cdot g^{-1}$ and 2 $m^2 \cdot g^{-1}$ expressed per gram of dry adsorbent.

Preparation of the Zeolite-based Adsorbents

A homogeneous mixture is prepared and 1600 g of crystals of NaX zeolite prepared according to the procedures described in Examples A or B are agglomerated with 350 g of kaolin (expressed as calcined equivalent) and 130 g of colloidal silica sold under the trade name Klebosol® 30 (containing 30% by weight of $SiO_2$ and 0.5% of $Na_2O$) with the amount of water allowing extrusion of the mixture. The loss on ignition of the paste before extrusion is 44%. Extrudates 1.6 mm in diameter are formed. The extrudates are dried overnight in a ventilated oven at 80° C. They are then calcined for 2 hours at 550° C. under a stream of nitrogen, and then for 2 hours at 550° C. under a stream of dry, decarbonated air and then crushed so as to recover grains with an equivalent diameter equal to 0.4 mm.

Example 1: (comparative)

Preparation of a Zeolite-based Adsorbent in Crushed Form with a Type X Zeolite, the Zeolite Crystals 1.0 µm in Size, and a Binder of Non-Zeolitized Kaolin Type Granules (200 g) obtained from the powder synthesized in Example B are exchanged using a 0.5 M barium chloride solution at 95° C. in 4 steps. At each step, the volume ratio of solution to mass of solid is 20 $ml \cdot g^{-1}$ and the exchange is continued for 4 hours each time. Between each exchange, the solid is washed several times so as to free it of the excesses of salt. It is then activated at a temperature of 250° C. for 2 hours under a stream of nitrogen.

The degree of barium exchange is 97% and the loss on ignition is 5.4%. The micropore volume and the outer surface area measured according to the t-plot method from the nitrogen adsorption isotherm at 77 K after degassing under vacuum at 400° C. for 10 hours are, respectively, 0.226 $cm^3 \cdot g^{-1}$ and 167 $m^2 \cdot g^{-1}$.

The total volume of the macropores and mesopores measured by mercury porosimetry is 0.32 $cm^3 \cdot g^{-1}$. The volume fraction of the macropores to the total volume of the macropores and mesopores is equal to 0.87.

The pore diameter distribution is determined from the analysis by mercury intrusion performed on the adsorbent and represented by the volume distribution dV/d log $D_{Hg}$ as a function of the apparent diameter of the pores $D_{Hg}$. The distribution shows a distinct peak in the region of the macropores corresponding to a unimodal distribution about a mode equal to about 350 nm.

The mechanical strength is also measured according to the method presented in the description of the invention. The pressure required to obtain 0.5% of fines is 2.2 MPa.

Example 2: (comparative)

Preparation of a Zeolite-based Adsorbent in Crushed Form with a Zeolite of X Type, the Zeolite Crystals 1.0 μm in Size, and a Binder of Zeolitized Kaolin Type Granules (200 g) obtained from the powder synthesized in Example B are placed in a glass reactor equipped with a jacket regulated at a temperature of 100° C.±1° C., and 1.5 L of an aqueous sodium hydroxide solution of concentration 1 M are then added and the reaction medium is left stirring for a time of 3 hours.

The agglomerates are then washed in 3 successive operations of washing with water followed by emptying the reactor. The washing efficiency is ensured by measuring the final pH of the washing waters, which is between 10.0 and 10.5.

These agglomerates are exchanged using a 0.5 M barium chloride solution at 95° C. in 4 steps. At each step, the volume ratio of solution to mass of solid is 20 ml·g−$^{1}$ and the exchange is continued for 4 hours each time. Between each exchange, the solid is washed several times so as to free it of the excesses of salt. It is then activated at a temperature of 250° C. for 2 hours under a stream of nitrogen.

The degree of barium exchange is 97% and the loss on ignition is 5.3%. The micropore volume and the outer surface area measured according to the t-plot method from the nitrogen adsorption isotherm at 77 K after degassing under vacuum at 400° C. for 10 hours are, respectively, 0.249 $cm^3 \cdot g^{-1}$ and 5 $m^2 \cdot g^{-1}$.

The total volume of the macropores and mesopores measured by mercury porosimetry is 0.29 $cm^3 \cdot g^{-1}$. The volume fraction of the macropores to the total volume of the macropores and mesopores is equal to 0.97.

The pore diameter distribution is determined from the analysis by mercury intrusion performed on the adsorbent and represented by the volume distribution dV/d log $D_{Hg}$ as a function of the apparent pore diameter $D_{Hg}$ (cf. FIG. 1). The distribution shows a distinct peak in the region of the macropores corresponding to a unimodal distribution about a mode equal to about 360 nm.

The content of non-zeolite-based phase is equal to 5% by weight, as measured by XRD, using as reference the starting zeolite crystals that have undergone the same barium exchange.

The mechanical strength is also measured according to the method presented in the description of the invention. The pressure required to obtain 0.5% of fines is 2.5 MPa.

Example 3: (comparative)

Preparation of a Zeolite-based Adsorbent in Crushed Form with a Zeolite of HPX Type, the Zeolite Crystals 4.5 μm in Size, and a Binder of Non-Zeolitized Kaolin Type Granules (200 g) obtained from the powder synthesized in Example A are exchanged using a 0.7 M barium chloride solution at 95° C. in 4 steps. At each step, the volume ratio of solution to mass of solid is 20 $ml \cdot g^{-1}$ and the exchange is continued for 4 hours each time. Between each exchange, the solid is washed several times so as to free it of the excesses of salt. It is then activated at a temperature of 250° C. for 2 hours under a stream of nitrogen.

The degree of barium exchange is 97% and the loss on ignition is 5.5%. The micropore volume and the outer surface area measured according to the t-plot method from the nitrogen adsorption isotherm at 77 K after degassing under vacuum at 400° C. for 10 hours are, respectively, 0.192 $cm^3 \cdot g^{-1}$ and 70 $m^2 \cdot g^{-1}$.

The total volume of the macropores and mesopores measured by mercury porosimetry is 0.33 $cm^3 \cdot g^{-1}$. The volume fraction of the macropores to the total volume of the macropores and mesopores is equal to 0.6.

The mechanical strength is also measured according to the method presented in the description of the invention. The pressure required to obtain 0.5% of fines is 2.1 MPa.

The pore diameter distribution is determined from the analysis by mercury intrusion performed on the adsorbent and represented by the volume distribution dV/d log $D_{Hg}$ as a function of the apparent pore diameter $D_{Hg}$ in FIG. 1. The distribution shows a peak and a shoulder in the region of the macropores, describing a bimodal distribution with a first mode at about 140 nm and a second in the region of the very small macropores, at about 55 nm.

Example 4 (according to the invention)

Preparation of a Zeolite-based Adsorbent in Crushed Form with Crystals of HPX Type 4.5 μm in Size, and a Binder of Zeolitized Kaolin Type Granules (200 g) obtained from the powder synthesized in Example A are placed in a glass reactor equipped with a jacket regulated at a temperature of 100° C.±1° C., and 1.5 L of an aqueous sodium hydroxide solution of concentration 1 M are then added and the reaction medium is left stirring for a time of 3 hours.

The agglomerates are then washed in 3 successive operations of washing with water followed by emptying the reactor. The washing efficiency is ensured by measuring the final pH of the washing waters, which is between 10.0 and 10.5.

These agglomerates are exchanged using a 0.5 M barium chloride solution at 95° C. in 4 steps. At each step, the volume ratio of solution to mass of solid is 20 $ml \cdot g^{-1}$ and the exchange is continued for 4 hours each time. Between each exchange, the solid is washed several times so as to free it of the excesses of salt. It is then activated at a temperature of 250° C. for 2 hours under a stream of nitrogen.

The degree of barium exchange is 96% and the loss on ignition is 5.3%. The micropore volume and the outer surface area measured according to the t-plot method from the nitrogen adsorption isotherm at 77 K after degassing under vacuum at 400° C. for 10 hours are, respectively, 0.260 $cm^3 \cdot g^{-1}$ and 12 $m^2 \cdot g^{-1}$.

The total volume of the macropores and mesopores measured by mercury porosimetry is 0.29 $cm^3 \cdot g^{-1}$. The volume fraction of the macropores to the total volume of the macropores and mesopores is equal to 0.9.

The pore diameter distribution is determined from the analysis by mercury intrusion performed on the adsorbent and represented by the volume distribution dV/d log $D_{Hg}$ as a function of the apparent pore diameter $D_{Hg}$ in FIG. 1. The distribution shows a distinct peak in the region of the macropores corresponding to a unimodal distribution about a mode equal to about 190 nm.

FIG. 1 represents the pore diameter distribution curves determined from the analysis by mercury intrusion performed on the adsorbents of Examples 2 to 4.

The content of non-zeolite-based phase is equal to 5% by weight, as measured by XRD, using as reference the starting zeolite crystals that have undergone the same barium exchange.

The mechanical strength is also measured according to the method presented in the description of the invention. The pressure required to obtain 0.5% of fines is 2.5 MPa.

Example 5

A breakthrough test (frontal chromatography) is then performed on these adsorbents to evaluate their efficiency. The amount of adsorbent used for this test is about 34 g.

The procedure for obtaining the breakthrough curves is as follows:

- filling of the column with the sieves and insertion in the test bench,
- filling with the desorption solvent at room temperature,
- gradual increase to the adsorption temperature under a stream of solvent (5 $cm^3$/min),
- injection of solvent at 30 $cm^3$/min when the adsorption temperature is reached,
- solvent/feedstock permutation to inject the feedstock (30 $cm^3 \cdot min^{-1}$);
- the injection of the feedstock is then maintained for a time sufficient to reach thermodynamic equilibrium (i.e. until the concentration of solvent in the effluent is zero), and
- collection and analysis of the breakthrough effluent.

The desorption solvent used is para-diethylbenzene. The composition of the feedstock is as follows:

- para-xylene: 45% by weight
- meta-xylene: 45% by weight
- isooctane: 10% by weight (this is used as a tracer for estimating the non-selective volumes and does not participate in the separation).

The test is performed with an adsorption temperature of 175° C. The pressure is sufficient for the feedstock to remain in the liquid phase, i.e. 1.5 MPa. The surface velocity (flow rate/column cross section) of circulation of the liquid at the test temperature is about 1.3 $cm \cdot s^{-1}$ for all of the tests.

The selectivity for para-xylene relative to meta-xylene is calculated by material balance. The breakthrough results are given in Table 1 below:

TABLE 1

| Adsorbent | PX/MX selectivity | Adsorption capacity (%) | EHTP (%) | CI | Mechanical strength |
|---|---|---|---|---|---|
| Example 1 (comparative) | 3.35 | 14.2 | 6.3 | 7.6 | 2.2 |
| Example 2 (comparative) | 3.52 | 17.4 | 8.4 | 7.3 | 2.5 |
| Example 3 (comparative) | 2.66 | 13.4 | 2.6 | 13.7 | 2.1 |
| Example 4 (invention) | 3.19 | 17.6 | 3.7 | 15.2 | 2.5 |

Key
PX = Para-Xylene;
MX = Meta-Xylene
Adsorption capacity expressed in % ($cm^3$ of $C_8$-aromatics adsorbed per $cm^3$ of column)
EHTP = Equivalent height of theoretical plates measured on para-xylene expressed in % of column length $$CI = \frac{\text{selectivity} \times \text{capacity}}{\text{EHTP}}$$

Relative to the results obtained with the adsorbent of Examples 1 and 2, a marked improvement in the mass transfer on the adsorbent of Example 4 is found, reflected by the considerably reduced equivalent height of theoretical plates.

Relative to the results obtained with the adsorbent of Example 3, a marked improvement in the selectivity for para-xylene with respect to meta-xylene (+17%) and a marked increase in the adsorption capacity are found for the adsorbent of Example 4.

The CI index combining all of these parameters, capacity, selectivity and EHTP, makes it possible to evaluate the impact of the compromise between selectivity, capacity and mass transfer: the higher the index, the better the compromise. It is noted that the CI indices calculated on the adsorbents based on HPX crystals, namely on the adsorbents of Examples 3 and 4 (Example 4 being according to the invention), are very markedly superior to the indices calculated on the adsorbents of Examples 1 and 2.

The highest calculated CI index is obtained on the adsorbent of Example 4 according to the invention, and, consequently, this adsorbent will be the most efficient for the separation of para-xylene.

The zeolite-based adsorbent according to the invention combines good mechanical strength, good adsorption selectivity for para-xylene, a high adsorption capacity and rapid transportation of molecules within the adsorbent.

What is claimed is:

1. An adsorbent comprising a zeolite-based phase and a non-zeolite-based phase, wherein said adsorbent:

has an outer surface area of less than or equal to 30 $m^2 \cdot g^{-1}$, a pore diameter distribution, determined by mercury intrusion according to standard ASTM D 4284-83 and expressed by the volume distribution dV/d log $D_{Hg}$, wherein $D_{Hg}$ is the apparent pore diameter and V is the pore volume, the mode of which is between 100 nm and 250 nm, limits inclusive, and the zeolite-based phase comprises at least one zeolite of FAU structure of X type.

2. The adsorbent according to claim 1, wherein the pore diameter distribution corresponds to a unimodal distribution.

3. The adsorbent according to claim 1, having a micropore volume, evaluated via the t-plot method from the nitrogen adsorption isotherm at a temperature of 77 K, which is greater than 0.200 $cm^3 \cdot g^{-1}$.

4. The adsorbent according to claim 1, wherein the adsorbent has a content of non-zeolite-based phase between 2% and 8% by weight relative to the total weight of the adsorbent.

5. The adsorbent according to claim 1, further comprising barium or barium and potassium.

6. The adsorbent according to claim 1, having macropores and the mesopores, wherein a total volume contained in the macropores and the mesopores as measured by mercury intrusion according to standard ASTM D4284-83 is between $0.15\ cm^3 \cdot g^{-1}$ and $0.5\ cm^3 \cdot g^{-1}$, limits inclusive.

7. The adsorbent according to claim 6 having a ratio defined as (macropore volume)/(macropore volume+mesopore volume) of between 0.2 and 1, limits inclusive.

8. The adsorbent according to claim 1, further having an Si/Al atomic ratio of between 1.00 and 1.50, limits inclusive.

9. A process for preparing the adsorbent according to claim 1, comprising the steps of:

a) agglomerating crystals of at least one FAU zeolite having an outer surface area as measured by nitrogen adsorption, of greater than $20\ m^2 \cdot g^{-1}$, limits inclusive, with a binder and also with an amount of water which allows the forming of an agglomerated material, followed by drying and calcination of the agglomerated material;

b) carrying out zeolitization of all or part of the binder by placing the agglomerated material obtained in step a) in contact with an aqueous basic solution, optionally in the presence of at least one structuring agent;

c) optionally, removing the structuring agent optionally present;

d) carrying out cationic exchange(s) of the agglomerated material of step b) or c) by placing the agglomerated material in contact with a solution of barium ions or of barium ions and potassium ions;

e) optionally, carrying out additional cationic exchange of the agglomerated material of step d) by placing the agglomerated material in contact with a solution of potassium ions;

f) washing and drying of the agglomerated material obtained in step d) or e), at a temperature of between 50° C. and 150° C.; and g) producing the zeolite-based adsorbent by activating the agglomerated material obtained in step f) under a stream of a gas selected from the group consisting of oxidizing gases and inert gases, wherein the gas is at a temperature of between 100° C. and 400° C.

10. The process according to claim 9, wherein the agglomeration binder used in step a) contains at least one zeolitizable clay.

11. The process according to claim 9 wherein the FAU zeolite crystals used during the agglomeration step (step a) have a number-mean diameter of between 1 μm and 20 μm, limits inclusive.

12. The process according to claim 9 wherein the FAU zeolite used in step a) is a hierarchically porous FAU zeolite.

13. A process, comprising using an adsorbent according to claim 1 as an adsorption agent in:

separating C8 aromatic isomer fractions or,
separating substituted toluene isomers or,
separating cresols, or
separating polyhydric alcohols.

14. A process for the gas-phase or liquid-phase separation of xylene isomers using at least one adsorbent according to claim 1.

15. A process for separating para-xylene from a feedstock of aromatic isomer fractions containing 8 carbon atoms, using, as para-xylene adsorption agent, an adsorbent according to claim 1.

16. The process according to claim 15, wherein the process is performed in a counter-current simulated moving bed adsorption unit, under the following operating conditions:

number of beds: 4 to 24;
number of zones: at least 4 operating zones, each being located between a feed point and a withdrawal point;
temperature between 100° C. and 250° C.;
pressure between the bubble pressure of xylenes (or of toluene when toluene is chosen as desorbent) at the process temperature and 3 MPa;
ratio of the flow rates of desorbent to feedstock to be treated: 0.7 to 2.5;
recycling rate between 2 and 12,
cycle time, corresponding to the time between two injections of desorbent onto a given bed: between 4 and 25 minutes.

17. The process according to claim 16, wherein the desorbent is toluene or para-diethylbenzene.

18. The process according to claim 16 wherein a water content in the inlet streams constituted by the feedstock and/or desorbent streams is adjusted to between 20 ppm and 150 ppm.

19. The process according to claim 10, wherein the one zeolitizable clay is chosen from the group consisting of kaolins, kaolinites, nacrites, dickites, halloysites and metakaolins, and mixtures thereof.

20. The adsorbent according to claim 1 having a micropore volume, evaluated via the t-plot method from the nitrogen adsorption isotherm at a temperature of 77 K, which is between $0.205\ cm^3 \cdot g^{-1}$ and $0.300\ cm^3 \cdot g^{-1}$.

21. The adsorbent according to claim 1 having a micropore volume, evaluated via the t-plot method from the nitrogen adsorption isotherm at a temperature of 77 K, which is between $0.205\ cm^3 \cdot g^{-1}$ and $0.290\ cm^3 \cdot g^{-1}$.

* * * * *